(12) United States Patent
Chiu et al.

(10) Patent No.: US 7,459,557 B2
(45) Date of Patent: Dec. 2, 2008

(54) SUBSTITUTED ISOINDOLE-1,3-DIONES

(75) Inventors: George Chiu, Bridgewater, NJ (US); Peter J. Connolly, New Providence, NJ (US); Jessica J. Liu, Three Bridges, NJ (US); Steven A. Middleton, Flemington, NJ (US); Virginia L. Pulito, Flemington, NJ (US); Shengjian Li, Belle Mead, NJ (US)

(73) Assignee: Janssen Pharmaceutica N.V., Beerse (BG)

( * ) Notice: Subject to any disclaimer, the term of this patent is extended or adjusted under 35 U.S.C. 154(b) by 0 days.

(21) Appl. No.: 11/451,196

(22) Filed: Jun. 12, 2006

(65) Prior Publication Data
US 2007/0093500 A1    Apr. 26, 2007

Related U.S. Application Data

(60) Provisional application No. 60/692,121, filed on Jun. 20, 2005.

(51) Int. Cl.
C07D 209/48    (2006.01)
C07D 487/04    (2006.01)

(52) U.S. Cl. .................. 544/362; 544/373; 514/253.04; 514/254.08

(58) Field of Classification Search .................. None
See application file for complete search history.

(56) References Cited

OTHER PUBLICATIONS

Vippagunta et al Advanced Drug Delivery Reviews, vol. 48, pp. 3-26 (2001).*
Wesolowska et al. Polish Journal of Pharmacology, vol. 54, pp. 391-399 (2002).*
Chapple, British Journal of Urology, vol. 81, Suppl. 1, pp. 34-47 (1998).*
Harrison et al., "Molecular characterization of $\alpha_1$- and $\alpha_2$ adrenoceptors", Trends Pharmacol Sci; 1991; 62-67.
Morrow and Creese,"Characterization of $\alpha_1$-Adrenergic Receptor Subtypes in Rat Brain: A Reevaluation of [$^3$H] WB4104 and [$^3$H] Prazosin Binding", Mol. Pharmacol; 1986; 29: 3201-330;.
Minneman et al., "Comparison of $\alpha_1$-Adrenergic Receptor Subtypes Distinguished by Chlorethylclonidine and WB 4101", Mol. Pharmacol; 1988; 33:509-514.
Schwinn et al., "Molecular Cloning and Expression of the cDNA for a Novel $\alpha_{1B}$-Adrenergic Receptor", J Biol Chem; 1992; 267:21936-21945.
Ramarao et al., "Genomic Organization and Expression of the Human $\alpha_{1B}$-Adrenergic Receptor", J Biol Chem; 267:21936-21945.
Bruno et al., "Molecular Cloning and Sequencing of a cDNA Encoding a Human $\alpha_{1A}$-Adrenergic Receptor", Biochem Biophys Res Commun; 1991; 179: 1485-1490.
Goetz et al., "BMY 7378 is a selective antagonist of the D subtype of $\alpha_1$-adrenoceptors", Eur J Pharmacol; 1995; 272:R5-R6.
Caine, "The present role of alpha-adrenergic blockers in the treatment of benign prostatic hypertrophy", J Urol; 1986; 136: 1-4.
Lepor, "Localization of the $\alpha_{1A}$-adrenoceptor in the human prostate", J. Urol. 1995,154, 2096-2099.
Perlberg et al., "Adrenergic Response of Bladder Muscle in Prostatic Obstruction," Urology; 1982; 20:524-527.
Restorick and Mundy,"The density of cholinergic and alpha and beta adrenergic receptors in the normal and hyper-reflexic human detrusor", Br J Urol; 1989; 63: 32-35.
Smith and Chapple, "In Vitro Response of Human Bladder Smooth Muscle in Unstable Obstructed Male Bladders: A Study of Pathophysiological Causes," Neurolog Urodyn; 1994; 12: 414-415.
Walden et al., "Localization of mRNA and receptor binding sites for the $\alpha_{1A}$-adrenoceptor subtype in the rat, monkey and human urinary bladder and prostate", J Urol; 1997; 157: 1032-1038.
Malloy et al., "$\alpha_1$-Adrenoceptor Receptor Subtypes in Human Detrusor", J Urol; 1998; 160: 937-943.
Piascik and Perez, "$\alpha_1$-Adrenergic Receptors: New Insights and Directions", J Pharmacol Exp Ther; 2001; 298: 403-410.
Danuser and Thor, "Inhibition of central sympathetic and somatic outflow to the lower urinary tract of the cat by the $\alpha_1$-adrenergic receptor antagonist prazosin", J Urol; 1995; 153: 1308-1312.
Ramage and Wyllie, "A comparison of the effects of doxazosin and terazosin on the spontaneous sympathetic drive to the bladder and related organs in anaesthetized cats", Eur J Pharmacol; 1995; 294: 645-650.

(Continued)

Primary Examiner—Emily Bernhardt
(74) Attorney, Agent, or Firm—Laura Donnelly

(57) ABSTRACT

The present invention relates to substituted isoindole-1,3-dione compounds of Formula (I)

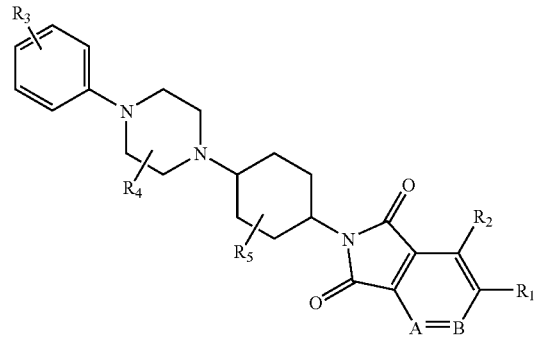

and pharmaceutically acceptable forms thereof, as $\alpha_{1a}/\alpha_{1d}$ adrenoceptor modulators for the treatment of benign prostatic hypertrophy and lower urinary tract symptoms. The present invention also relates to pharmaceutical compositions comprising said new compounds, new processes to prepare these new compounds and new uses as a medicine as well as methods of treatment.

1 Claim, No Drawings

OTHER PUBLICATIONS

Ishizuka et al., "Micturition in conscious rats with and without bladder outlet obstruction: role of spinal $\alpha_1$-adrenoceptors", Br J Pharmacol; 1996; 117:962-966.

Persson et al., "Spinal and peripheral mechanisms contributing to hyperactive voiding in spontaneously hypertensive rats", Am J Physiol; 1998; 275:R1366-1373.

Steers et al., "The spontaneously hypertensive rat: insight into the pathogenesis of irritative symptoms in benign prostatic hyperplasia and young anxious males", 1999; Exp Physiol, 1999; 84:137-147.

Smith et al., $\alpha_1$-Adrenergic receptors in human spinal cord: specific localized expression of mRNA encoding "$\alpha_1$-adrenergic receptor subtypes at four distinct levels", Mol Brain Res; 1999; 63:254-261.

Abrams et al. "Tamsulosin, a selective $\alpha_{1C}$-adrenoceptor antagonist: a randomized, controlled trial in patients with benign prostatic 'obstruction' (symptomatic BPH)", Br J Urol; 1995; 76:325-336.

Lepor, "Phase III multicenter placebo-controlled study of tamsulosin in benign prostatic hyperplasia", Urology; 1998; 51:892-900.

Rudner et al., "Subtype Specific Regulation of Human Vascular $\alpha_1$-Adrenergic Receptors by Vessel Bed and Age", Circulation; 199; 100:2336-2343.

Lepor, "Long-term evaluation of tamsulosin in benign prostatic hyperplasia: placebo-controlled, double-blind extension of phase III trial", Urology; 1998; 51:901-906.

Heaton, "The serious side of lifestyles issues in urology", Brit J Urol Int; 2003; 92:875-879.

* cited by examiner

SUBSTITUTED ISOINDOLE-1,3-DIONES

CROSS REFERENCE TO RELATED APPLICATIONS

This present application claims benefit of U.S. Provisional Patent Application Ser. No. 60/692,121, filed Jun. 20, 2005, which is incorporated herein by reference in its entirety and for all purposes.

FIELD OF THE INVENTION

The present invention relates to new compounds, more particularly new substituted isoindole-1,3-diones as selective $\alpha_{1a}/\alpha_{1d}$ adrenoreceptor modulators for the treatment of benign prostatic hypertrophy and/or lower urinary tract symptoms. The present invention also relates to pharmaceutical compositions comprising said new compounds, new processes to prepare these new compounds, to the use of these compounds as $\alpha_{1a}/\alpha_{1d}$ adrenoreceptor modulators and new uses as a medicine as well as methods of treatment.

BACKGROUND OF THE INVENTION

The adrenergic receptors (ARs), through which norepinephrine and epinephrine exert their biological activities, are targets for many therapeutically important drugs. The $\alpha_1$-ARs play a dominant role in control of smooth muscle contraction and are important in control of blood pressure, nasal congestion, prostate function, and other processes (Harrison et al., Trends Pharmacol Sci; 1991; 62-67). The $\alpha_1$-ARs were originally classified by pharmacological profiling into two subtypes, $\alpha_{1a}$ and $\alpha_{1b}$ (Morrow and Creese, Mol. Pharmacol; 1986; 29: 231-330; Minneman et al., Mol. Pharmacol; 1988; 33:509-514). Three genes encoding different $\alpha_1$-AR subtypes ($\alpha_{1a}$, $\alpha_{1b}$, and $\alpha_{1d}$) have been cloned for a number of species, including human (Schwinn et al., J. Biol Chem; 1990; 265: 8183-8189; Ramarao et al., J Biol Chem; 1992; 267:21936-21945; Bruno et al., Biochem Biophys Res Commun; 1991; 179: 1485-1490). These three cloned $\alpha_1$-ARs are best differentiated from one another on the basis of the relative binding affinities of a series of antagonist compounds. There is general agreement that the $\alpha_{1a}$- and $\alpha_{1b}$-ARs correspond to the pharmacologically defined $\alpha_{1a}$- and $\alpha_{1b}$-ARs, while the functional role of the $\alpha_{1d}$-AR is less clear, although it appears to mediate contraction of certain blood vessels (Goetz et al., Eur J Pharmacol; 1991; 272:R5-R6). Like other ARs, the $\alpha_1$-ARs are members of the G-protein coupled receptor super family, and in most cells the primary functional response to activation of all $\alpha_1$-AR subtypes is an increase in intracellular $Ca^{2+}$.

Benign prostatic hyperplasia (BPH) is a non-malignant enlargement of the prostate and is the cause of lower urinary tract symptoms (LUTS) in a large segment of the elderly male population. Symptoms such as straining, hesitancy, dribbling, weak stream, and incomplete emptying are classified as voiding or obstructive symptoms. Obstructive symptoms are primarily due to pressure upon the urethra from the physical mass of the enlarged prostate gland (the static component) and the increased tone of the smooth muscle of the prostate stroma and bladder neck (the dynamic component) (Caine, J Urol; 1986; 136: 1-4). Irritative or storage symptoms associated with BPH are frequency, urgency, nocturia, dysuria, and burning sensation. Patients feel that these symptoms are more disturbing than the obstructive symptoms. As the urine flow is reduced, due to the bladder outlet obstruction, the wall around the bladder base thickens and becomes hyperactive.

Functional studies have established that prostate smooth muscle tone is maintained through $\alpha_1$-ARs and that these receptors mediate the dynamic component of obstruction. $\alpha_1$-AR antagonists have successfully been used to treat the obstructive symptoms associated with BPH (Jardin et al., Scientific Communications Int; 1998; pp 559-632). Furthermore, the $\alpha_{1a}$-AR subtype comprises the majority of $\alpha_1$-ARs in human prostatic smooth muscle and has been shown to mediate contraction in this tissue. Originally introduced as antihypertensive agents, $\alpha_1$-AR antagonists have become increasingly important in the management of BPH. $\alpha_1$-AR antagonists reduce smooth muscle tone in the prostate and lower urinary tract, thereby relaxing the bladder outlet and increasing urinary flow. The major disadvantage of non-selective $\alpha_1$-blockers is their adverse effect profile, particularly vasodilatation leading to dizziness, postural hypotension, asthenia, and occasionally syncope. For this reason, it would be desirable to block $\alpha_1$-ARs in the lower urinary tract without antagonizing the $\alpha_1$-ARs responsible for maintaining vascular tone.

A number of factors can be involved in lower urinary tract symptoms. Adrenergic stimulation of the bladder results in relaxation due to $\beta$-ARs, which dominate over contraction-mediating $\alpha_1$-ARs. Bladder contraction is primarily mediated by muscarinic receptors. Some studies indicate that the contribution from $\alpha_1$-ARs increases in hyperactive bladders due to bladder outlet obstruction or other conditions (Perlberg et al., Urology; 1982; 20:524-527); Restorick and Mundy, Br J Urol; 1989; 63: 32-35). However another study finds no change in $\alpha_1$-AR receptor function between normal and hypertrophic bladder due to outlet obstruction (Smith and Chapple, Neurolog Urodyn; 1994; 12: 414-415). It remains unclear, which $\alpha_1$-AR is dominant in the human bladder. One study reported a predominance of the $\alpha_{1a}$ subtype mRNA in the bladder dome, base, and trigone (Walden et al., J Urol; 1997; 157: 414-415). Another report found that the $\alpha_{1d}$ subtype is present as 66% of the $\alpha_1$-ARs at both the mRNA and protein levels, while the $\alpha_{1a}$ subtype is present as 34% of the total, with no evidence of the $\alpha_{1b}$ subtype (Malloy et al., J Urol; 1998; 160: 937-943). Drugs that selectively antagonize only the $\alpha_{1a}$-AR subtype appear to have little effect upon the irritative symptoms of BPH. Ro-70004, a $\alpha_{1a}$ subtype-selective compound was reported to be discontinued in clinical studies when it was found to have poor efficacy in treating these symptoms (Blue et al., Abstract 5$^{th}$ International Consultation on BPH (Jun. 25-28) 2000). $\alpha_{1d}$-ARs may be involved in mediating the irritative symptoms; however, the location of these $\alpha_{1d}$-ARs is unknown (Piascik and Perez, J Pharmacol Exp Ther; 2001; 298: 403-410).

Studies have demonstrated Central Nervous Systems (CNS) inhibitory effects of $\alpha_1$ antagonists upon the sympathetic and somatic outflow to the bladder in cats (Danuser and Thor, J Urol; 1995; 153: 1308-1312; Ramage and Wyllie, Eur J Pharmacol; 1995; 294: 645-650). Intrathecally administered doxazosin caused a decrease in micturition pressure in both normal rats and rats with bladder hypertrophy secondary to outlet obstruction (Ishizuka et al., Br J Pharmacol; 1996; 117:962-966). These effects may be due to a reduction in parasympathetic nerve activity in the spinal cord and ganglia. Other studies used spontaneously hypertensive rats, which have overactive bladders, to demonstrate that $\alpha_1$-AR antagonism only given intrathecally caused a return to normal micturition (Persson et al., Am J Physiol; 1998; 275:R1366-1373, Steers et al. 1999; Exp Physiol; 84:137-147.). Antagonists administered intra-arterially near the bladder, or ablation of peripheral noradrenergic nerves, had no effect upon the bladder overactivity in these animals, indicating that $\alpha_1$-ARs in the spinal cord control the bladder activity. Spinal $\alpha_1$-ARs may be important targets for pharmacological treatment of BPH symptoms in humans as well. All three $\alpha_1$-AR subtype mRNAs are found throughout the human spinal cord, however the aid subtype mRNA is present at twice the level of the other subtypes, particularly in the ventral sacral motor neurons and autonomic parasympathetic pathways. (Stafford-Smith et al., Mol Brain Res; 1998; 63:234-261). There may be clinical advantages to the pharmacological blockade of the $\alpha_{1d}$-ARs in the CNS in reducing BPH symptoms.

Antagonism of $\alpha_{1d}$-ARs in the CNS and bladder may be an important activity in reducing the irritative or filling symptoms of BPH and improving patient symptom scores. Tamsulosin (Flomax®, Yamanuchi and Boehringer Ingelheim) is a $\alpha_1$-AR antagonist, which is about 15-fold selective for the $\alpha_{1a}$ and $\alpha_{1d}$ subtypes over the $\alpha_{1b}$ subtype. Large clinical trials of BPH patients with tamsulosin showed improvement in both obstructive and irritative symptoms, however, cardiovascular and erectile dysfunction side effects were seen (Abrams et al. Br J Urol; 1995; 76:325-336; Chapple et al., Eur Urol; 1996; 29:155-167; Lepor, Urology; 1998; 51:892-900). Patients treated with non-selective $\alpha_1$ antagonists also have improvement in both obstructive and irritative symptoms, although the risk of vascular side effects is greater. Generally, the $\alpha_{1a}$ subtype predominates in arteries at the mRNA and protein levels, while all three subtypes are found in veins. The particular vessel bed is important in that the $\alpha_{1a}$ is the subtype found primarily in the splanchnic and coronary arteries, while the $\alpha_{1d}$ subtype is the predominant subtype found in the aorta. The $\alpha_1$-AR subtypes in the vasculature have been found to change with age. Contraction of the mammary artery is mediated by both $\alpha_{1a}$ and $\alpha_{1b}$ subtypes. The number of $\alpha_1$ receptors in the mammary artery doubles with age; however, the $\alpha_{1b}$ subtype increases to a greater extent than the $\alpha_{1a}$ subtype (Raudner et al., Circulation; 1999; 100:2336-2343). The $\alpha_{1b}$ subtype may play a greater role in vascular tone in elderly patients. This suggests that an $\alpha_{1a}$ and $\alpha_{1d}$-selective antagonist may have less effects upon the vasculature in elderly BPH patients, resulting in fewer cardiovascular side effects than are seen with non-selective $\alpha_1$ antagonists, but provide relief from both obstructive and irritative symptoms.

A uroselective, cardiovascular-sparing $\alpha_1$-AR antagonist would be expected to provide symptomatic relief of BPH comparable to currently marketed non-selective agents such as terazosin/Hytrin®, doxazosin/Cardura®, alfuzosin/Xatral®/Uroxatral® and weakly selective tamsulosin/Flomax®/Harnal®, without the undesirable side effects of postural hypotension, dizziness, and syncope. Ejaculatory dysfunction, or retrograde ejaculation, is a side effect seen in 10 to 35% of patients using tamsulosin (Lepor, Urology; 1998; 51:901-906; Andersson and Wyllie, Brit J Urol Int; 2003; 92:876-877). This activity has been attributed to tamsulosin antagonism at the 5-$HT_{1a}$ receptor. This often leads to discontinuation of treatment. Furthermore, the non-selective $\alpha_1$-AR antagonists and tamsulosin are contraindicated for use in conjunction with PDE inhibitors. There is likely to be high co-morbidity between LUTS and erectile dysfunction patients. Patients being treated for LUTS with the current $\alpha_1$-AR blockers will find that they are excluded from using PDE inhibitors. An $\alpha_1$-AR antagonist with a receptor subtype binding profile, which is selective for the $\alpha_{1a}$ and $\alpha_{1d}$ subtypes, but with relatively little antagonism of the $\alpha_{1b}$ subtype may effectively treat both obstructive and irritative symptoms of BPH. Such a compound is likely to have a low cardiovascular side effect profile and allow for use in conjunction with PDE inhibitors. Also low binding activity at the 5-$HT_{1a}$ receptor is likely to reduce the incidence of ejaculatory side effects.

LUTS also develop in women of a certain age. As in men, LUTS in women include both filling symptoms such as urgency, incontinence and nocturnia, and voiding symptoms such as weak stream, hesitancy, incomplete bladder emptying and abdominal straining. The presence of this condition both in men and women suggests that at least part of the aetiology may be similar in the two sexes.

Accordingly, there is a need to provide $\alpha_{1a}/\alpha_{1d}$ adrenoreceptor modulator compounds; in particular, mono or dual selective $\alpha_{1a}/\alpha_{1d}$ adrenoreceptor modulator compounds; more particularly, mono or dual selective $\alpha_{1a}/\alpha_{1d}$ adrenoreceptor antagonist compounds, in other words compounds that interact with either one (i.e., "mono") or both (i.e., "dual") the $\alpha_{1a}$ or/and $\alpha_{1d}$ adrenoreceptor but do not interact (or at least interact substantially less) with the $\alpha_{1b}$ adrenoreceptor. The compounds of this invention are believed to be more efficacious drugs mainly for BPH/LUTS patients, and at the same time these compounds should show less unwanted side effects than the existing pharmaceuticals.

SUMMARY OF THE INVENTION

The present invention provides a substituted isoindole-1, 3-dione compound of Formula (I)

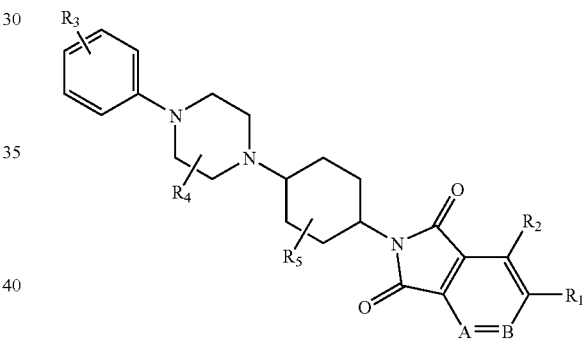

and pharmaceutically acceptable forms thereof, wherein
$R_1$ and $R_2$ is each selected from the group consisting of
(1) hydrogen,
(2) $NH_2$, $NH(C_{1-8}alkyl)$ or $N(C_{1-8}alkyl)_2$,
(3) cyano,
(4) halogen,
(5) hydroxy, and
(6) nitro,
-A=B- is selected from the group consisting of —C($R_6$)=C($R_7$)—, —N=C($R_7$)— and —C($R_6$)=N—,
$R_6$ and $R_7$ is each selected from the group consisting of
(1) hydrogen,
(2) $NH_2$, $NH(C_{1-8}alkyl)$ or $N(C_{1-8}alkyl)_2$,
(3) cyano,
(4) halogen,
(5) hydroxy, and
(6) nitro,
alternatively, $R_6$ and $R_7$ are combined to form an aryl ring system fused at A and B on the compound of Formula (I), wherein the aryl ring system is optionally substituted with one or more substituents selected from the group consisting of (1) $NH_2$, $NH(C_{1-8}alkyl)$ or $N(C_{1-8}alkyl)_2$,
(2) cyano,
(3) halogen,
(4) hydroxy, and
(5) nitro, $R_3$ is up to four optionally present substituents independently selected from the group consisting of
(1) $C_{1-8}alkyl$,
(2) $C_{1-8}alkoxy$,
(3) $C_{1-8}alkyl(C_{1-8}alkoxy)$,
(4) $C_{1-8}alkyl(halogen)_{1-17}$,
(5) $C_{1-8}alkoxy(halogen)_{1-17}$,
(6) $NH_2$, $NH(C_{1-8}alkyl)$ or $N(C_{1-8}alkyl)_2$,
(7) halogen,
(8) hydroxy, and
(9) $C_{1-8}alkoxy(C_{3-8}cycloalkyl)$, and $R_4$ and $R_5$ is each hydrogen or is each up to four substituents independently selected from the group consisting of $C_{1-8}alkyl$, $C_{1-8}alkoxy$, $NH_2$, $NH(C_{1-8}alkyl)$, $N(C_{1-8}alkyl)_2$, cyano, halogen, oxo and nitro.

The present invention also provides pharmaceutical compositions comprising a effective amount of any of the compounds of Formula (I) described in the present application and a pharmaceutical acceptable carrier.

An example of the invention is a pharmaceutical composition made by combining any of the compounds of Formula (I) described in the present application and a pharmaceutically acceptable carrier.

Another illustration of the invention is a process for making a pharmaceutical composition comprising combining any of the compounds described in the present application and a pharmaceutically acceptable carrier.

It is an aspect of the present invention to provide compounds that are modulators for the $\alpha_{1a}$-AR and $\alpha_{1d}$-AR subtypes. In this aspect, the modulator compounds of the present invention are AR antagonists. Specifically in this aspect, the compounds are mono or dual inhibitors for the $\alpha_{1a}$-AR or/and $\alpha_{1d}$-AR subtypes. More specifically in this aspect, the compounds are selective mono or dual inhibitors.

The present invention further provides a method for treating a patient suffering from a disease or disorder mediated by mono or dual selective $\alpha_{1a}/\alpha_{1d}$ adrenoreceptor modulator compounds comprising administering to the patient an effective amount of the compound of Formula (I) and pharmaceutically acceptable forms thereof, wherein In another aspect, the invention is directed to methods for treating or preventing a disease or disorder mediated by mono or dual selective $\alpha_{1a}/\alpha_{1d}$ adrenoreceptor antagonists such as, but not limited to, contractions of the prostate, bladder and other organs of the lower urinary tract without substantially affecting blood pressure. In this aspect, the method comprises administering the mono or dual selective $\alpha_{1a}/\alpha_{1d}$ adrenoreceptor antagonist compounds of the present invention or a pharmaceutically acceptable form thereof to a patient suffering from contractions of the bladder and other organs of the lower urinary tract in an amount effective for the particular use.

Another aspect of the present invention is to provide a method for treating a patient suffering from Benign Prostatic Hyperplasia (BPH). In this aspect, the method comprises administering an effective amount of the inhibitor compounds of the present invention or a pharmaceutically acceptable form thereof to a patient suffering from BPH.

Another aspect of the present invention is to provide a method for treating a patient suffering from lower-urinary-tract-symptoms (LUTS), which include, but are not limited to, filling symptoms, urgency, incontinence and nocturia, as well as voiding problems such as weak stream, hesitancy, intermittency, incomplete bladder emptying and abdominal straining. In this aspect, the method comprises administering an effective amount of the inhibitor compounds of the present invention or a pharmaceutically acceptable form thereof to a patient suffering from LUTS.

A further aspect of the present invention is the use of the inhibitor compounds of the present invention or a pharmaceutically acceptable form thereof as a medicine. In this aspect, the use of the inhibitor compound or pharmaceutically acceptable form thereof includes the manufacture of a medicament for the treatment of an $\alpha_{1a}/\alpha_{1d}$ adrenoreceptor mediated disease and, in particular, for the treatment of BPH and/or LUTS.

In another aspect of the present invention, the method for treating a patient suffering from BPH and/or LUTS includes administering an effective amount of a combination product comprising an inhibitor compound of the present invention in combination with a BPH and/or LUTS therapeutic agent. The BPH and/or LUTS therapeutic agent includes a 5α-reductase agent (such as finasteride or durasteride and the like or mixtures thereof), a NK-1 inhibitor, an anti-androgen receptor agonist, an androgen receptor antagonist, a selective androgen receptor modulators, a PDE inhibitor, a urinary incontinence drugs (e.g. anti-muscarinics) or a 5HT-receptor modulator.

DETAILED DESCRIPTION OF THE INVENTION

It should be understood that pharmaceutically acceptable forms for compounds described and listed herein are meant to include all hydrates, solvates, polymorphs and pharmaceutically acceptable salts thereof. It should also be understood that unless otherwise indicated compounds of Formula (I) are meant to comprise the stereochemically isomeric forms thereof.

An example of the present invention includes a compound of Formula (I) and pharmaceutically acceptable forms thereof, wherein $R_1$ and $R_2$ is each selected from the group consisting of hydrogen and halogen.

An example of the present invention includes a compound of Formula (I) and pharmaceutically acceptable forms thereof, wherein -A=B- is selected from the group consisting of —C($R_6$)=C($R_7$)—, —N=C($R_7$)— and —C($R_6$)=N—.

An example of the present invention includes a compound of Formula (I) and pharmaceutically acceptable forms thereof, wherein $R_6$ and $R_7$ is each selected from the group consisting of hydrogen and halogen.

An example of the present invention includes a compound of Formula (I) and pharmaceutically acceptable forms thereof, wherein $R_6$ and $R_7$ are combined to form an aryl ring system fused at A and B on the compound of Formula (I), wherein the aryl ring system is optionally substituted with one or more halogen substituents.

An example of the present invention includes a compound of Formula (I) and pharmaceutically acceptable forms thereof, wherein $R_3$ is up to four optionally present substituents independently selected from the group consisting of
(1) $C_{1-8}alkyl$,
(2) $C_{1-8}alkoxy$,
(3) $C_{1-8}alkoxy(halogen)_{1-17}$, and
(4) $C_{1-8}alkoxy(C_{3-8}cycloalkyl)$.

An example of the present invention includes a compound of Formula (I) and pharmaceutically acceptable forms thereof, wherein $R_3$ is up to four optionally present $C_{1-8}alkoxy$ substituents.

An example of the present invention includes a compound of Formula (I) and pharmaceutically acceptable forms thereof, wherein $R_4$ and $R_5$ is each hydrogen.

An example of the present invention includes a compound of Formula (I) selected from a compound of Formula (Ia):

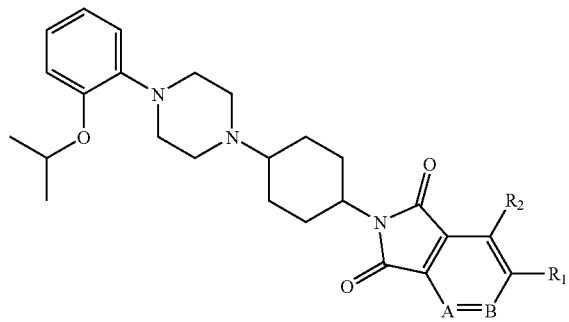

and pharmaceutically acceptable forms thereof, wherein -A=B- is selected from the group consisting of —C($R_6$)=C($R_7$)—, —N=C($R_7$)— and —C($R_6$)=N—; $R_6$ and $R_7$ is each selected from the group consisting of hydrogen and halogen; and, $R_1$ and $R_2$ is each selected from the group consisting of hydrogen and halogen.

An example of the present invention includes a compound of Formula (I) selected from a compound of Formula (Ia1):

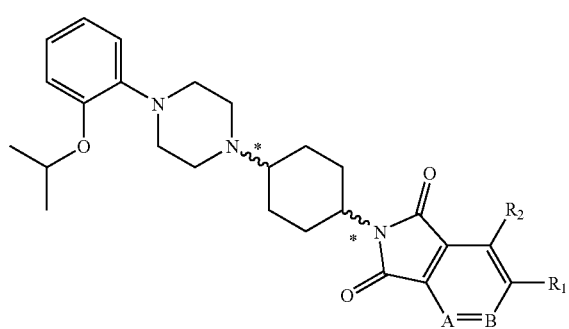

and pharmaceutically acceptable forms thereof, wherein -A=B-, $R_1$ and $R_2$ are dependently selected from:

| Cpd | *Config | —A=B— | $R_1$ | $R_2$ |
|---|---|---|---|---|
| 1 | cis/trans | —C(F)=C(F)— | F | F |
| 2 | cis/trans | —CH=C(Cl)— | Cl | H |
| 3 | trans | —C(F)=CH— | H | H |
| 4 | cis | —C(F)=CH— | H | H |
| 5 | cis/trans | —N=CH— | H | H |
| 6 | cis/trans | —CH=N— | H | H |

An example of the present invention includes a compound of Formula (I) selected from a pound of Formula (Ib):

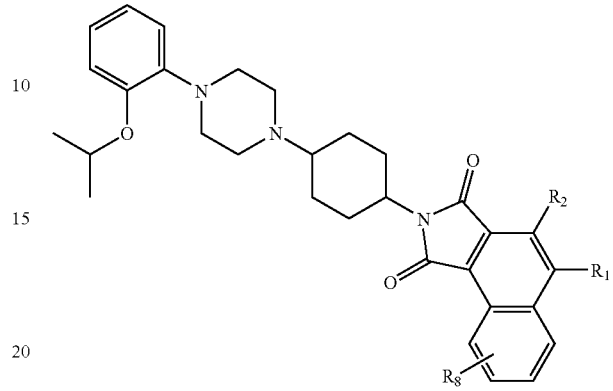

and pharmaceutically acceptable forms thereof, wherein $R_1$ and $R_2$ is each selected from the group consisting of hydrogen and halogen; and, $R_8$ is selected from the group consisting of hydrogen and halogen.

An example of the present invention includes a compound of Formula (Ib) selected from a compound of Formula (Ib1):

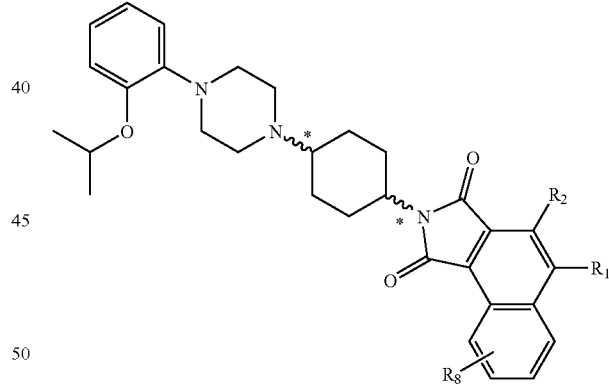

and pharmaceutically acceptable forms thereof, wherein $R_1$, $R_2$ and $R_8$ are dependently selected from:

| Cpd | *Config | $R_1$ | $R_2$ | $R_8$ |
|---|---|---|---|---|
| 7 | cis/trans | H | H | H |
| 8 | cis | H | H | 8-F |
| 9 | trans | H | H | 8-F |

Another example of the present invention includes a compound of Formula (I) and pharmaceutically acceptable forms thereof, wherein the compound is selected from the group consisting of:
Cpd 1
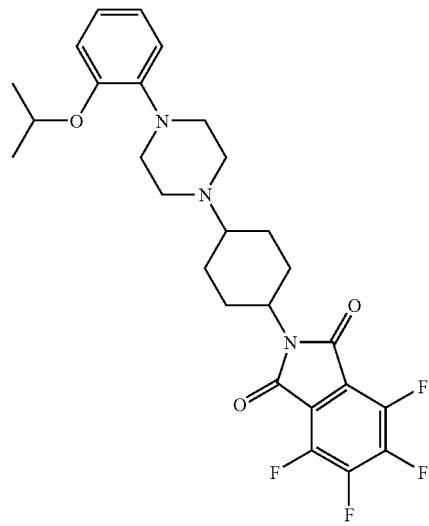
Cpd 2
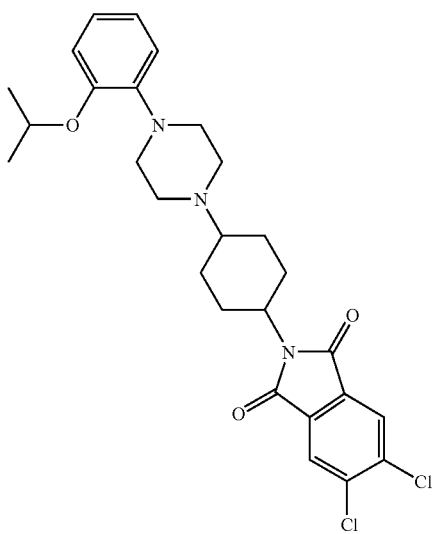
Cpd 3
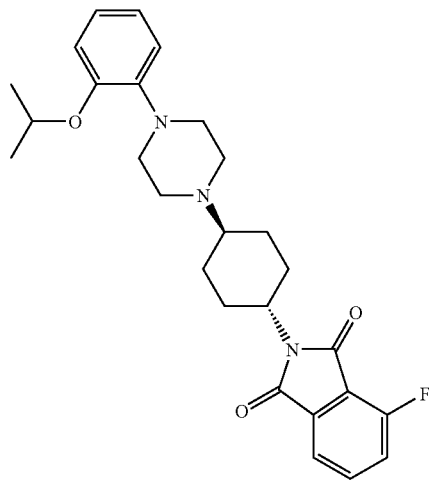
-continued
Cpd 4
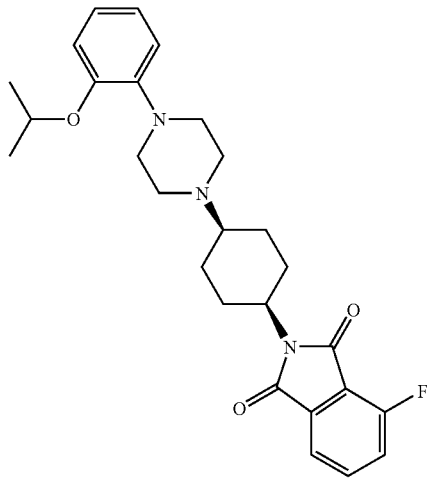
Cpd 5
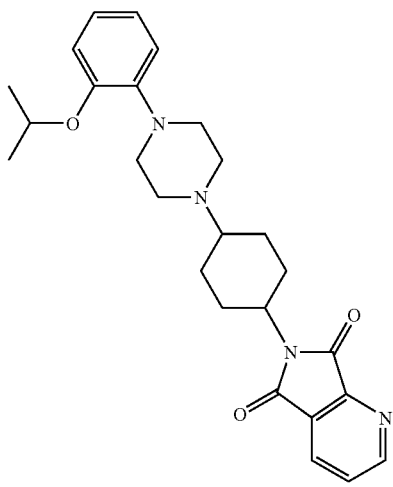
Cpd 6
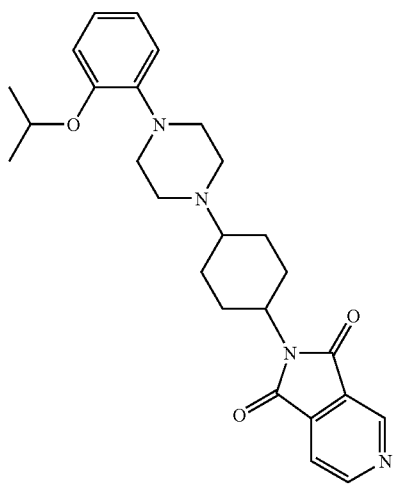

-continued

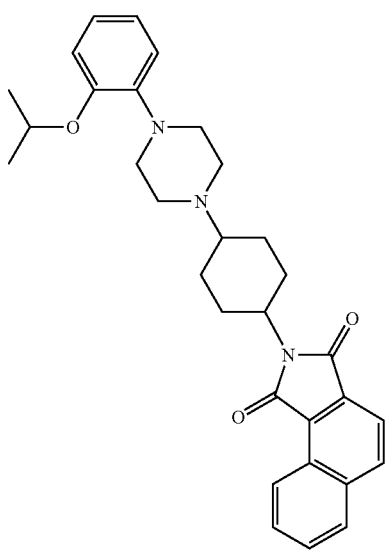
Cpd 7

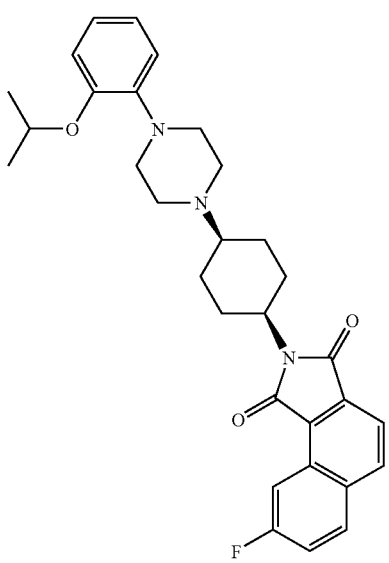
Cpd 8

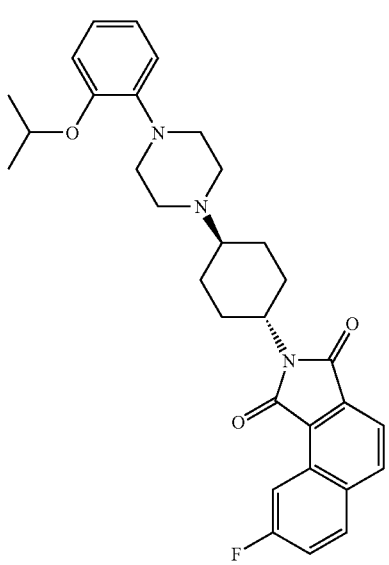
Cpd 9

Pharmaceutically Acceptable Forms

The compounds of the present invention may be present in the form of pharmaceutically acceptable salts. For use in medicines, the "pharmaceutically acceptable salts" of the compounds of this invention refer to non-toxic acidic/anionic or basic/cationic salt forms.

Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, fumaric acid, maleic acid, succinic acid, acetic acid, benzoic acid, citric acid, tartaric acid, carbonic acid or phosphoric acid.

Furthermore when the compounds of the present invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts. Thus, representative pharmaceutically acceptable salts include the following: acetate, benzenesulfonate, benzoate, bicarbonate, bisulfate, bitartrate, borate, bromide, calcium, camsylate (or camphosulphonate), carbonate, chloride, clavulanate, citrate, dihydrochloride, edetate, fumarate, gluconate, glutamate, hydrabamine, hydrobromine, hydrochloride, iodide, isothionate, lactate, malate, maleate, mandelate, mesylate, nitrate, oleate, pamoate, palmitate, phosphate/diphosphate, salicylate, stearate, sulfate, succinate, tartrate, tosylate.

Certain compounds of the Formula (I) may exist in various stereoisomeric or tautomeric forms and mixtures thereof. The present invention encompasses all such dual $\alpha_{1a}/\alpha_{1d}$ adrenoceptor inhibiting compounds, including active compounds in the form of essentially pure enantiomers, racemic mixtures, pure geometric isomers (such as cis and trans stereoisomers), mixtures of geometric isomers, and tautomers.

The present invention indeed contemplates compounds of various isomers and mixtures thereof. The term "isomer" refers to compounds that have the same composition and molecular weight but differ in physical and/or chemical properties. Such substances have the same number and kind of atoms but differ in structure. The structural difference may be in constitution (geometric isomers) or in an ability to rotate the plane of polarized light (optical isomers, or enantiomers).

The term "stereoisomer" refers to isomers of identical constitution that differ in the arrangement of their atoms in space. Enantiomers are stereoisomers wherein an asymmetrically substituted carbon atom acts as a chiral center. The term "chiral" refers to a molecule that is not superposable on its mirror image, implying the absence of an axis and a plane or center of symmetry. The term "enantiomer" refers to one of a pair of molecular species that are mirror images of each other and are not superimposable. The term "diastereomer" refers to stereoisomers that are not related as mirror images. The symbols "R" and "S" represent the configuration of substituents around a chiral carbon atom(s). The symbols "R*" and "S*" denote the relative configurations of of substituents around a chiral carbon atom(s). Where the compounds of the present application have at least one stereocenter, they accordingly exist as enantiomers. Where the compounds according to the present invention posses two or more stereocenters, they may additionally exist as diastereoisomers. It is to be understood that all such isomers and mixtures thereof are encompassed within the scope to the present invention.

The term "racemate" or "racemic mixture" refers to a compound of equimolar quantities of two enantiomeric species, wherein the compound is devoid of optical activity. The term "optical activity" refers to the degree to which a chiral molecule or nonracemic mixture of chiral molecules rotates the plane of polarized light.

The term "geometric isomer" refers to isomers that differ in the orientation of substituent atoms in relationship to a carbon-carbon double bond, to a cycloalkyl ring or to a bridged bicyclic system. Substituent atoms (other than H) on each side of a carbon-carbon double bond may be in an E or Z configuration. In the "E" (opposite sided) configuration, the substituents are on opposite sides in relationship to the carbon-carbon double bond; in the "Z" (same sided) configuration, the substituents are oriented on the same side in relationship to the carbon-carbon double bond. Substituent atoms (other than H) attached to a carbocyclic ring may be in a cis or trans configuration. In the "cis" configuration, the substituents are on the same side in relationship to the plane of the ring; in the "trans" configuration, the substituents are on opposite sides in relationship to the plane of the ring. Compounds having a mixture of "cis" and "trans" species are designated "cis/trans".

The compounds of the present invention may be prepared as individual isomers by either isomer-specific synthesis or resolved from an isomeric mixture. Conventional resolution techniques include forming the free base of each isomer of an isomeric pair using an optically active salt (followed by fractional crystallization and regeneration of the free base), forming an ester or amide of each of the isomers of an isomeric pair (followed by chromatographic separation and removal of the chiral auxiliary) or resolving an isomeric mixture of either a starting material or a final product using preparative TLC (thin layer chromatography) or a chiral HPLC column.

Furthermore, compounds of the present invention may have one or more polymorph or amorphous crystalline forms and as such are intended to be included in the scope of the invention. In addition, some of the compounds may form solvates with water (i.e., hydrates) or common organic solvents, and such are also intended to be encompassed within the scope of this invention.

Chemical Definitions

As used herein, the following terms are intended to have the following meanings (additional definitions are provided where needed throughout the Specification):

The term "$C_{1-8}$ alkyl," whether used alone or as part of a substituent group, means a straight or branched chain monovalent hydrocarbon alkyl radical or alkyldiyl linking group comprising from 1 to 8 carbon atoms, wherein the radical is derived by the removal of one hydrogen atom from a single carbon atom and the alkyldiyl linking group is derived by the removal of one hydrogen atom from each of two carbon atoms in the chain, such as, for example methyl, ethyl, 1-propyl, 2-propyl, 1-butyl, 2-butyl, tertiary butyl, 1-pentyl, 2-pentyl, 3-pentyl, 1-hexyl, 2-hexyl, 3-hexyl, 1-heptyl, 2-heptyl, 3-heptyl, 1-octyl, 2-octyl, 3-octyl and the like. Examples include $C_{1-8}$alkyl, $C_{1-6}$alkyl and $C_{1-4}$alkyl groups.

The term "$C_{1-8}$ alkoxy," whether used alone or as part of a substituent group, refers to an alkyl or alkyldiyl radical attached through an oxygen linking atom. Typical alkoxy groups comprising from 1 to 8 carbon atoms, such as, for example, methoxy, ethoxy, propoxy, butoxy, pentoxy, hexoxy, heptoxy, octoxy and the like. An alkoxy radical may be attached to a core molecule and further substituted where indicated. Examples include $C_{1-8}$alkoxy or $C_{1-4}$alkoxy groups.

The term "$C_{3-12}$ cycloalkyl," whether used alone or as part of a substituent group, refers to a saturated or partially unsaturated, monocyclic or polycyclic hydrocarbon ring system radical derived by the removal of one hydrogen atom from a single ring carbon atom. The term "$C_{3-8}$ cycloalkyl," whether used alone or as part of a substituent group, refers to a saturated or partially unsaturated, monocyclic or polycyclic hydrocarbon ring system radical derived by the removal of one hydrogen atom from a single ring carbon atom having 3 to 8 carbon atoms in the ring. Examples include $C_{5-8}$cycloalkyl, $C_{3-10}$cycloalkyl and the like. Typical cycloalkyl radicals include cyclopropyl, cyclobutyl, cyclopentyl, cyclohexyl, cycloheptyl, cyclooctyl, 1H-indenyl, indanyl, tetrahydro-naphthalenyl and the like.

The term "halogen" includes fluoro, chloro, bromo, and iodo.

The term "substituted," refers to a core molecule on which one or more hydrogen atoms have been replaced with one or more functional radical moieties. The number that is allowed by available valences limits the amount of substituents. Substitution is not limited to the core molecule, but may also occur on a substituent radical, whereby the substituent radical becomes a linking group.

The term "independently selected" refers to one or more substituents selected from a group of substituents variable group, wherein the selected substituents may be the same or different.

The term "dependently selected" refers to one or more substituents specified in an indicated combination of structure variables.

Therapeutic Use

In an example of therapeutic use, the compounds of the present invention are modulators for the $\alpha_{1a}$-AR and $\alpha_{1d}$-AR subtypes and are, thus, useful for the treatment of BPH and/or LUTS.

In another example of therapeutic use, the modulator compounds are agonists, inverse-agonists or antagonists for each of the $\alpha_{1a}$-AR and $\alpha_{1d}$-AR subtypes. In another example, the modulator compounds are selective agonists for each of the $\alpha_{1a}$-AR and $\alpha_{1d}$-AR subtypes. In another example, the modulator compounds are selective inverse-agonists for each of the $\alpha_{1a}$-AR and $\alpha_{1d}$-AR subtypes. In another example, the modulator compounds are selective antagonists for each of the $\alpha_{1a}$-AR and $\alpha_{1d}$-AR subtypes.

In another example of therapeutic use, the modulator compounds are agonists, inverse-agonists or antagonists for both the $\alpha_{1a}$-AR and $\alpha_{1d}$-AR subtypes. In another example, the modulator compounds are selective agonists for both the $\alpha_{1a}$-AR and $\alpha_{1d}$-AR subtypes. In another example, the modulator compounds are selective inverse-agonists for both the $\alpha_{1a}$-AR and $\alpha_{1d}$-AR subtypes. In another example, the modulator compounds are selective antagonists for both the $\alpha_{1a}$-AR and $\alpha_{1d}$-AR subtypes.

The binding affinities for instant compounds demonstrate selectivity as modulators. The specificity of binding affinities for instant compounds demonstrate selectivity as modulators for either the $\alpha_{1a}$-AR or $\alpha_{1d}$-AR subtype when compared to the binding affinities for other types of $\alpha_1$-ARs.

Furthermore, the binding affinities for instant compounds demonstrate selectivity as modulators for both the $\alpha_{1a}$-AR and $\alpha_{1d}$-AR subtypes when compared to the binding affinities for other types of $\alpha_1$-ARs.

Accordingly, the modulator compounds of the present invention are useful for treating, ameliorating or preventing a plurality of $\alpha_{1a}$-AR and $\alpha_{1d}$-AR mediated disorders or diseases. The usefulness of a compound of the present invention or pharmaceutical composition thereof as an $\alpha_{1a}$-AR or $\alpha_{1d}$-AR modulator or as a dual $\alpha_{1a}$ and $\alpha_{1d}$-AR modulator can be determined according to the methods disclosed herein.

The term "$\alpha_{1a}$-AR and $\alpha_{1d}$-AR mediated disorder or disease" means disorders or diseases such as, but not limited to, contractions of the prostate, bladder and other organs of the lower urinary tract with or without an effect on blood pressure. The scope of such use includes the treatment of BPH and/or LUTS.

The term "LUTS" means disorders or diseases such as, but not limited to, filling symptoms, urgency, incontinence and nocturia, as well as voiding problems such as weak stream, hesitancy, intermnittency, incomplete bladder emptying and abdominal straining.

The present invention thereby includes a method for treating, ameliorating or preventing an $\alpha_{1a}$-AR and $\alpha_{1d}$-AR mediated disorder or disease in a patient in need thereof comprising administering to the patient an effective amount of a compound of Formula (I) or pharmaceutical composition thereof.

The present invention thereby includes a method for treating, ameliorating or preventing BPH and/or LUTS in a patient in need of such treatment comprising administering to the patient an effective amount of a compound of Formula (I) or pharmaceutical composition thereof.

The term "patient" means an animal, preferably a mammal, most preferably a human, which has been the object of treatment, prevention, observation or experiment.

The term "administering" is to be interpreted liberally in accordance with the methods of the present invention. Such methods include therapeutically or prophylactically administering an effective amount of a composition or medicament of the present invention at different times during the course of a therapy or concurrently in a combination form. Prophylactic administration can occur prior to the manifestation of symptoms characteristic of an $\alpha_{1a}$ and/or $\alpha_{1d}$ adrenoreceptor mediated disorder or disease such that the disorder or disease is treated, ameliorated, prevented or otherwise delayed in its progression. The methods of the present invention are further to be understood as embracing all therapeutic or prophylactic treatment regimens used by those skilled in the art.

The term "effective amount" refers to that amount of active compound or pharmaceutical agent that elicits the biological or medicinal response in a tissue system, animal or human, that is being sought by a researcher, veterinarian, medical doctor, or other clinician, which includes treating, ameliorating or preventing the symptoms of a syndrome, disorder or disease being treated.

An effective amount of a compound of Formula (I) is in a range of from about 0.0002 mg/kg to about 2000 mg/kg of body weight per day.

In an example of the method for treating, ameliorating or preventing an $\alpha_{1a}$-AR and $\alpha_{1d}$-AR mediated disorder or disease described herein, the method includes treating a patient suffering from BPH and/or LUTS comprising administering to the patient an effective amount of a combination product comprising a compound of Formula (I) or pharmaceutical composition thereof in combination with a BPH and/or LUTS therapeutic agent.

The BPH and/or LUTS therapeutic agent includes a human testosterone 5α-reductase inhibitor agent or 5-α reductase isoenzyme 2 inhibitor agent (such as finasteride or durasteride and the like or mixtures thereof), a NK-1 inhibitor, an anti-androgen receptor agonist, an androgen receptor antagonist, a selective androgen receptor modulators, a PDE inhibitor, a urinary incontinence drugs (e.g. anti-muscarinics) or a 5HT-receptor modulator.

With regard to the method for administering a combination product, the term "effective amount" means that amount of the compound of Formula (I) or pharmaceutical composition thereof in combination with that amount of the therapeutic agent which have been adjusted to treat, ameliorate or prevent the symptoms of a syndrome, disorder or disease being treated.

As those skilled in the art will appreciate, the dosages of the compound of Formula (I) or pharmaceutical composition thereof and the therapeutic agent may be independently optimized and combined to achieve a synergistic result wherein the pathology is reduced more than it would be if either agent were used alone. In accordance with the method of the present invention, the individual components of the combination can be administered separately at different times during the course of therapy or concurrently in divided or single combination forms. The instant invention is therefore to be understood as embracing all such regimes of simultaneous or alternating treatment and the term "administering" is to be interpreted accordingly.

In solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogenous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention.

The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. An enteric layer can separate the two components. That enteric layer serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

As used herein, the term "composition" is intended to encompass a product comprising the specified ingredients in the specified amounts, as well as any product which results, directly or indirectly, from combination of the specified ingredients in the specified amounts.

An effective but non-toxic amount of the compound desired can be employed as a $\alpha_{1a}/\alpha_{1d}$ antagonistic agent. Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentration of drug within the range that yields efficacy without toxicity requires a regimen based on the kinetics of the drug's availability to target sites. This involves a consideration of the distribution, equilibrium and elimination of a drug.

Compounds of Formula (I) may be administered in any of the foregoing compositions and according to dosage regimens established in the art whenever inhibition of the human $\alpha_{1a}$-AR or $\alpha_{1a}$-AR is required. Such inhibition includes inhibition of the human $\alpha_{1a}$-AR or $\alpha_{1a}$-AR, selective inhibition of the human $\alpha_{1a}$-AR or $\alpha_{1a}$-AR, dual inhibition of the human $\alpha_{1a}$-AR and $\alpha_{1a}$-AR or selective, dual inhibition of the human $\alpha_{1a}$-AR and $\alpha_{1a}$-AR. The compounds of Formula (I) may be used alone at appropriate dosages defined by routine testing in order to obtain optimal antagonism of the human $\alpha_{1a}$-AR or $\alpha_{1a}$-AR while minimizing any potential toxicity.

The daily dosage of the products may be varied over a wide range from about 0.001 to about 3,000 mg per adult human per day. For oral administration, the compositions are preferably provided in the form of tablets containing 0.01, 0.05, 0.1, 0.5, 1.0, 2.5, 5.0, 10.0, 15.0, 25.0, 50.0 and milligrams of the active ingredient for the symptomatic adjustment of the dosage to the patient to be treated. A medicament typically contains from about 0.01 mg to about 500 mg of the active ingredient, preferably, from about 0.01 mg to about 3000 mg of active ingredient.

An effective amount of a compound of Formula (I) is a dosage level range of from about 0.0002 mg/kg to about 2000 mg/kg of body weight per day. In an example of the invention, the range is from about 0.001 to 10 mg/kg of body weight per day. In another example of the invention, the range is from about 0.001 mg/kg to 7 mg/kg of body weight per day. The compounds may be administered on a regimen of 1 to 4 times per day.

When compounds of Formula (I) are administered in a combination product, the compound of Formula (I) or pharmaceutical composition thereof and the therapeutic agent may be co-administered or sequentially administered whereby the effects of BPH and/or LUTS is treated, ameliorated or prevented.

The effective amount of the therapeutic agent selected from a human testosterone 5α-reductase inhibitor agent or 5-α reductase isoenzyme 2 inhibitor agent (such as finasteride or durasteride and the like or mixtures thereof), a NK-1 inhibitor, an anti-androgen receptor agonist, an androgen receptor antagonist, a selective androgen receptor modulators, a PDE inhibitor, a urinary incontinence drugs (e.g. antimuscarinics) or a 5HT-receptor modulator is a dosage level range of from about 0.0002 mg/kg to about 20 mg/kg of body weight per day. Preferably, the range is from about 0.001 to 10 mg/kg of body weight per day. More preferably, the range is from about 0.001 mg/kg to 7 mg/kg of body weight per day.

In one example of the combination product, the therapeutic agent is finasteride. The method for administering a combination product further comprises administering to the patient an effective amount of a compound of Formula (I) or pharmaceutical composition thereof in combination with finasteride.

The effective amount of finasteride administered in such a combination product is a dosage level range of from about 0.01 mg per day to about 50 mg per day. Preferably, the range is from about 0.2 mg per day to about 10 mg per day. More preferably, the range is from about 1 mg per day to about 7 mg per day. Most preferably, the dosage level is about 5 mg per day.

Synthetic Methods

Representative compounds of the present invention can be synthesized in accordance with the general synthetic schemes described below and are illustrated more particularly in the specific synthetic examples that follow. The general schemes and specific examples are offered by way of illustration; the invention should not be construed as being limited by the chemical reactions and conditions expressed. The methods for preparing the various starting materials used in the schemes and examples are well within the skill of persons versed in the art. No attempt has been made to optimize the yields obtained in any of the example reactions. One skilled in the art would know how to increase such yields through routine variations in reaction times, temperatures, solvents and/or reagents.

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, 3rd Edition, John Wiley & Sons, 1999. The protecting groups may be removed at a convenient subsequent stage using methods known in the art.

Synthetic Routes

Where the processes for the preparation of the compounds according to the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

The terms used in describing the invention are commonly used and known to those skilled in the art. Some reagents are referred to as a chemical formula. Other reagents are referred to as abbreviations known to persons skilled in the art. When used herein, the following abbreviations have the indicated meanings:

| | |
|---|---|
| Boc | tert-butoxy carbonyl |
| Cpd | compound |
| DCM or $CH_2Cl_2$ | dichloromethane |
| EtOAc or AcOEt | ethyl acetate |
| HOAc | acetic acid |
| LCMS | Liquid Chromatography Mass Spectrometry |
| min/hr(s)/d(s) | minute/hour(s)/day(s) |
| MS | Mass Spectrum in m/z (M + H$^+$) |
| m/z | mass/charge |
| NaB(OAc)$_3$H | sodium triacetoxyborohydride |
| Ret. | retention time |
| RT/rt/r.t. | room temperature |
| TFA | trifluoroacetic acid |
| TLC | Thin Layer Chromatography |

Specific compounds which are representative of the invention may be prepared as per the following examples offered by way of illustration and not by way of limitation. No attempt has been made to optimize the yields obtained in any of the reactions. One skilled in the art would know how to increase such yields through routine variations in reaction times, temperatures, solvents and/or reagents. Additional compounds may be made according to the synthetic methods of the present invention by one skilled in the art, differing only in possible starting materials, reagents and conditions used in the instant methods.

Scheme A

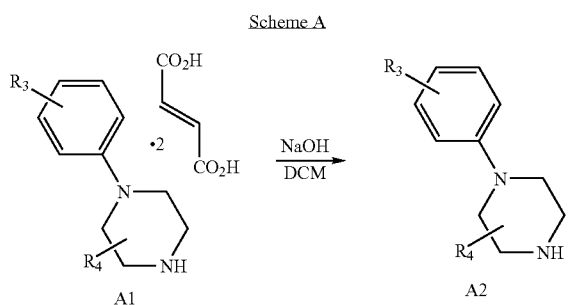

An $R_3$ and $R_4$ substituted 1-phenyl-piperazine difumarate Compound A1 is taken up in a solvent (such as DCM and the like) and treated with a base (such as 1N NaOH and the like) to form two layers. The aqueous layer is extracted (using a solvent such as DCM and the like) and the combined organic extracts are dried (such as with $K_2CO_3$, $Na_2SO_4$ and the like). The solvent is evaporated from the dry solution to provide a substituted 1-phenyl-piperazine Compound A2.

One or more of the $R_3$ or $R_4$ substituents (as previously described) for the Compound A1 starting material may be amenable for further substitution using various reagent(s) and reaction conditions, thus enabling the preparation of other compounds that are representative of the invention both as shown herein and further by one skilled in the art.

Compound A2, an $R_5$ substituted (4-oxo-cyclohexyl)-carbamic acid tert-butyl ester Compound A3, a reducing agent (such as $NaB(OAc)_3H$ and the like), with or without a catalytic amount of an acid (such as HOAc and the like) and a dry solvent (such as anhydrous DCM and the like) are mixed together at r.t. to form a slurry. The mixture is stirred under a nitrogen atmosphere for about 18 hrs until Compound A3 is no longer detected (using TLC and/or LCMS). The mixture is diluted with a solvent (such as DCM, AcOEt and the like), sequentially washed (with water, $NaHCO_3$ or $NH_4Cl$ (saturated) and the like) and dried (such as over $Na_2SO_4$). The solvent is evaporated from the dry solution to produce a crude product which is purified via flash chromatography (on a silica gel column, using AcOEt or an AcOEt/hexane mixture as eluent) to provide a substituted [4-(4-phenyl-piperazin-1-yl)-cyclohexyl]-carbamic acid tert-butyl ester Compound A4 as a mixture of cis and trans isomers.

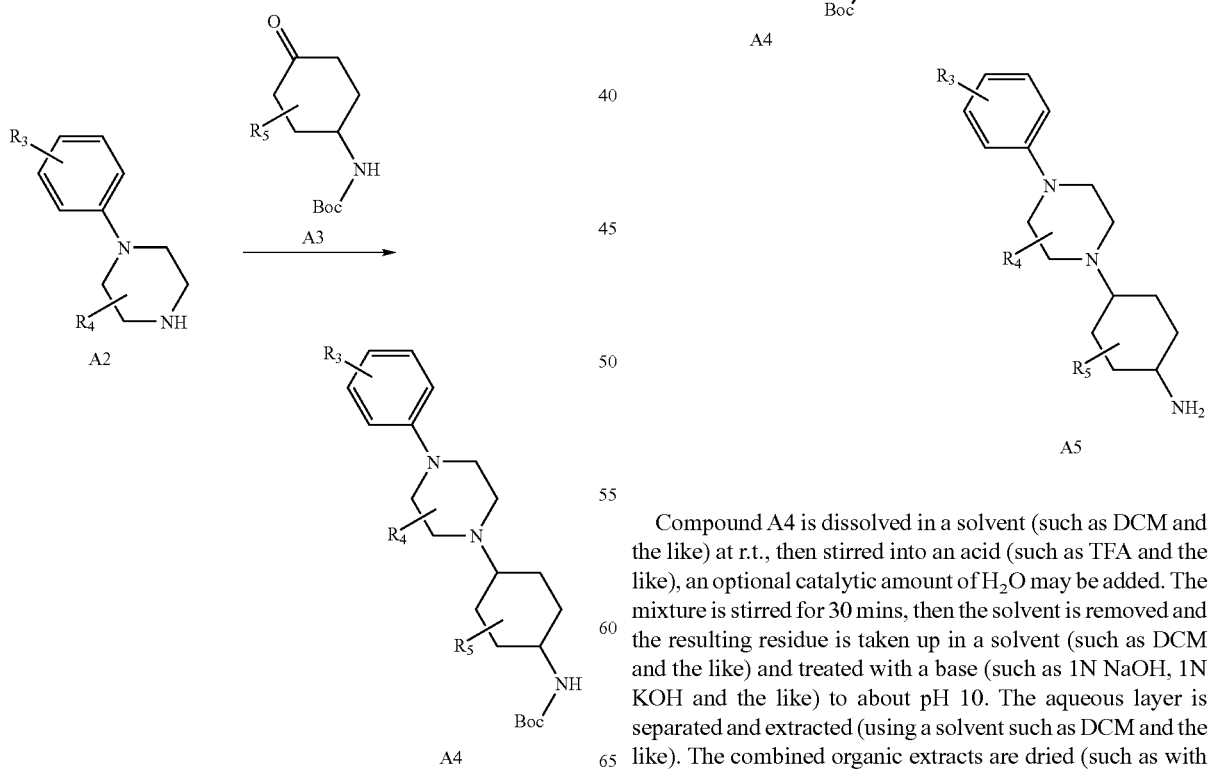

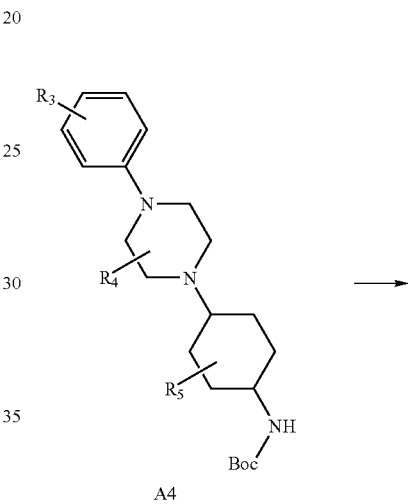

Compound A4 is dissolved in a solvent (such as DCM and the like) at r.t., then stirred into an acid (such as TFA and the like), an optional catalytic amount of $H_2O$ may be added. The mixture is stirred for 30 mins, then the solvent is removed and the resulting residue is taken up in a solvent (such as DCM and the like) and treated with a base (such as 1N NaOH, 1N KOH and the like) to about pH 10. The aqueous layer is separated and extracted (using a solvent such as DCM and the like). The combined organic extracts are dried (such as with $K_2CO_3$, $Na_2SO_4$ and the like) to provide a substituted 4-(4- phenyl-piperazin-1-yl)-cyclohexylamine Compound A5 as a crude product which is used in the next step without further purification.

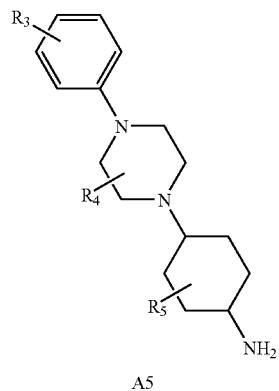

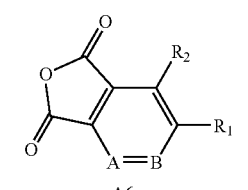

MeOH/DCM mixture as eluent) to provide a compound of Formula I as a cis and trans isomer mixture.

The substituents for Compound A3, Compound A6 or the compound of Formula I may be further substituted either before or after deprotection using various reaction materials, reagent(s) and conditions, thus enabling the preparation of other compounds that are representative of the invention by one skilled in the art.

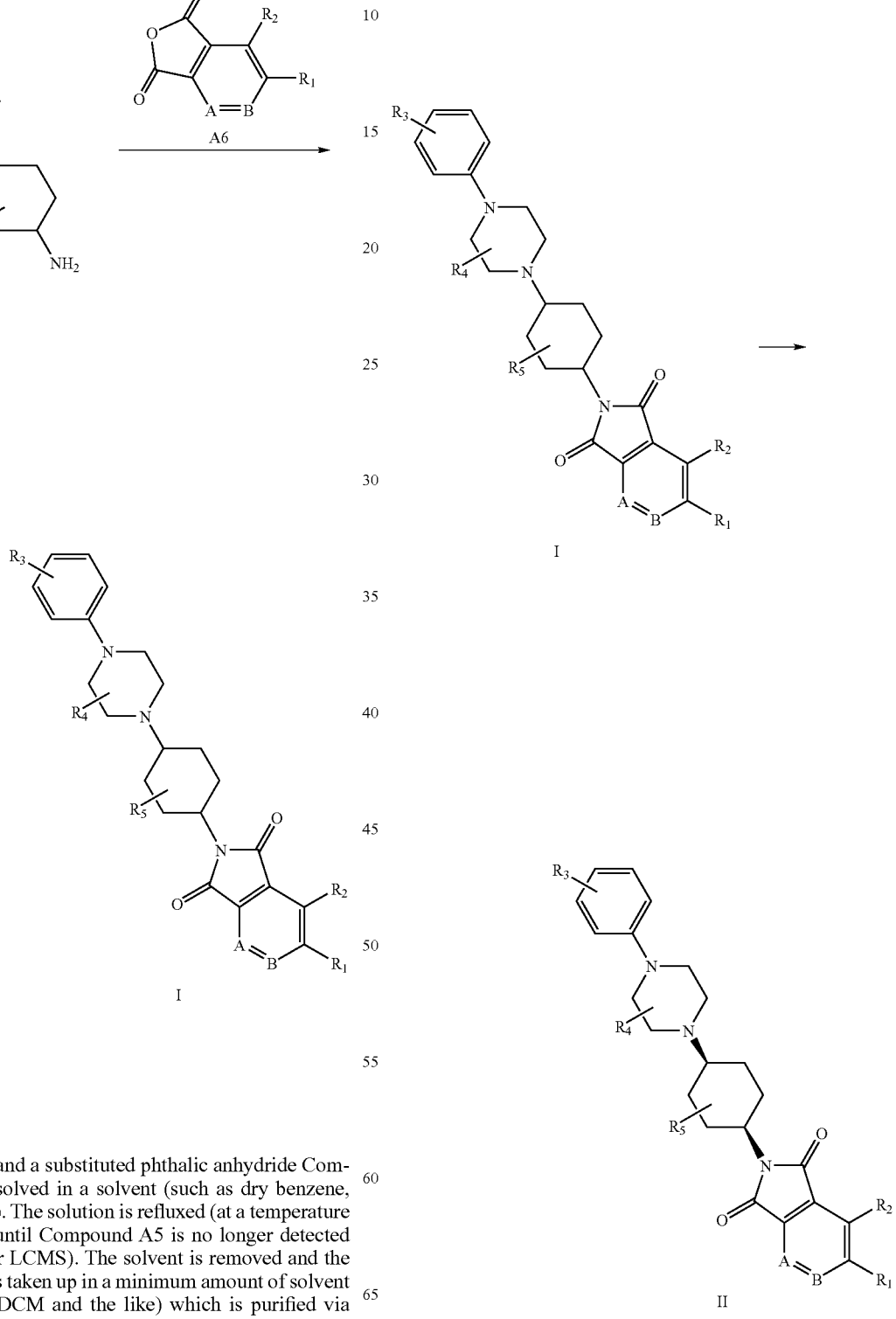

Compound A5 and a substituted phthalic anhydride Compound A6 are dissolved in a solvent (such as dry benzene, DCM and the like). The solution is refluxed (at a temperature of about 80° C.) until Compound A5 is no longer detected (using TLC and/or LCMS). The solvent is removed and the resulting residue is taken up in a minimum amount of solvent (such as MeOH, DCM and the like) which is purified via preparative plate chromatography (on silica gel, using -continued

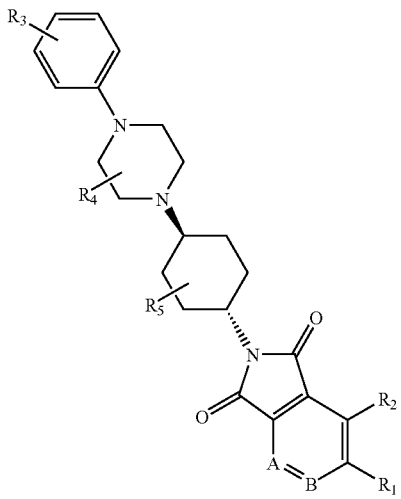

III

The compound of Formula I may be separated into a plurality of isomeric forms via chromatographic techniques such as preparative TLC (using an eluent mixture such as 5% MeOH/DCM and the like), e.g., a cis isomer such as the compound of Formula II is relatively less polar and a trans isomer such as the compound of Formula III is relatively more polar.

The compound of Formula II and the compound of Formula III may be converted into a plurality of stereoisomeric compounds that are representative of the invention by using art-known functional group transformations.

The compound of Formula II and the compound of Formula III may be converted into a plurality of pharmaceutically acceptable salt forms by reaction with an appropriate acid or base.

EXAMPLE 1

4,5,6,7-tetrafluoro-2-{4-[4-(2-isopropoxy-phenyl)-piperazin-1-yl]-cyclohexyl}-isoindole-1,3-dione (Cpd 1)

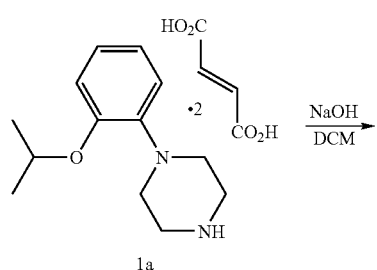

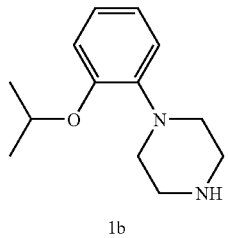

1b

Difumarate 1-(2-isopropoxy-phenyl)-piperazine Compound 1a (10 g, 29.7 mmol) was mixed with dichloromethane (DCM, 100 mL) and treated with 1N NaOH (80 mL). The two resulting layers were separated and the aqueous layer was extracted with DCM (20 mL×3) and the combined organic extracts were dried over $K_2CO_3$. The free base 1-(2-isopropoxy-phenyl)-piperazine Compound 1b (6.5 g) was obtained by evaporating the solvent from the filtered dry solution using a rotary evaporator.

Compound 1b (3.00 g, 13.6 mmol), (4-oxo-cyclohexyl)-carbamic acid tert-butyl ester Compound 1c (2.90 g, 13.6 mmol), $NaB(OAc)_3H$ (8.6 g, 40.8 mmol), HOAc (1 mL) and anhydrous DCM (80 mL) were mixed together at room temperature. The resulting white slurry was stirred under a nitrogen atmosphere for 18 hrs and became a yellowish solution.

When the presence of Compound 1c was no longer detected by TLC (100% AcOEt), the reaction mixture was diluted with DCM (80 mL), sequentially washed with H₂O and NH₄Cl (sat.) and dried over Na₂SO₄. The solvent was evaporated from the filtered dry solution using a rotary evaporator to obtain a crude product which was purified via flash chromatography (100% AcOEt, silica gel) to provide {4-[4-(2-isopropoxy-phenyl)-piperazin-1-yl]-cyclohexyl}-carbamic acid tert-butyl ester Compound 1d (5.43 g, 13.02 mmol, 96%) as a white sticky oil. LC-MS (2.85 mins) m/z 418.2 (M⁺H); $^1$H NMR (CDCl₃, TMS) δ 1.38 (d, J=6.0 Hz, 6 H), 1.46 (s, 9 H), 1.50-2.40 (m, 8 H), 2.74 (br s, 4 H), 3.13 (br s, 4 H), 3.20-4.400 (m, 2 H), 4.20-4.90 (m, 2 H), 6.80-7.05 (m, 4 H).

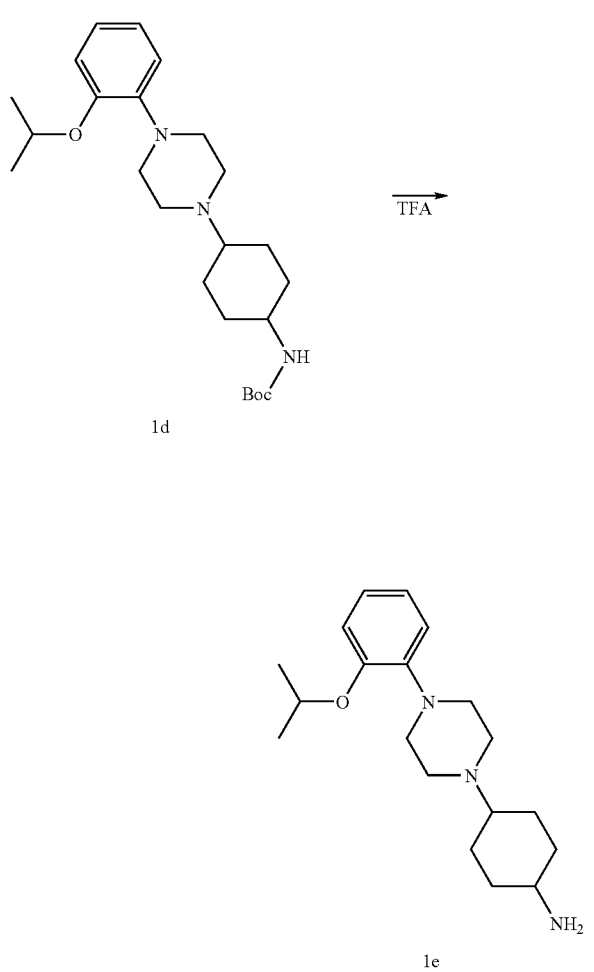

Compound 1d (5.43 g, 13.0 mmol) was dissolved into DCM (25 mL) at r.t. The resulting yellowish clear solution was stirred with TFA (10 mL) for 30 mins. The solvent was removed using a rotary evaporator and the resulting yellow residue was mixed with DCM (80 mL) and treated with 1N KOH to pH 10. The aqueous layer was separated and extracted with DCM (20 mL×3). The combined organic extracts were dried over K₂CO₃/Na₂SO₄ to provide 4-[4-(2-isopropoxy-phenyl)-piperazin-1-yl]-cyclohexylamine Compound 1e (3.08 g, 74.6%) as a white sticky oil, which was used directly in the next step without further purification. LC-MS (2.258 mins) m/z 318.2 (M⁺H); $^1$H NMR (CDCl₃, TMS) δ 1.05-1.20 (m, 1H), 1.20-1.45 (m, 3H), 1.30 (d, J=6.0 Hz, 6H), 1.48-1.76 (m, 4H), 1.83-2.02 (m, 2H), 2.20-2.50 (m, 1H), 2.55-2.85 (m, 4H), 2.95-3.25 (m, 5H), 4.54-4.60 (m, 1H), 6.80-6.92 (m, 4H).

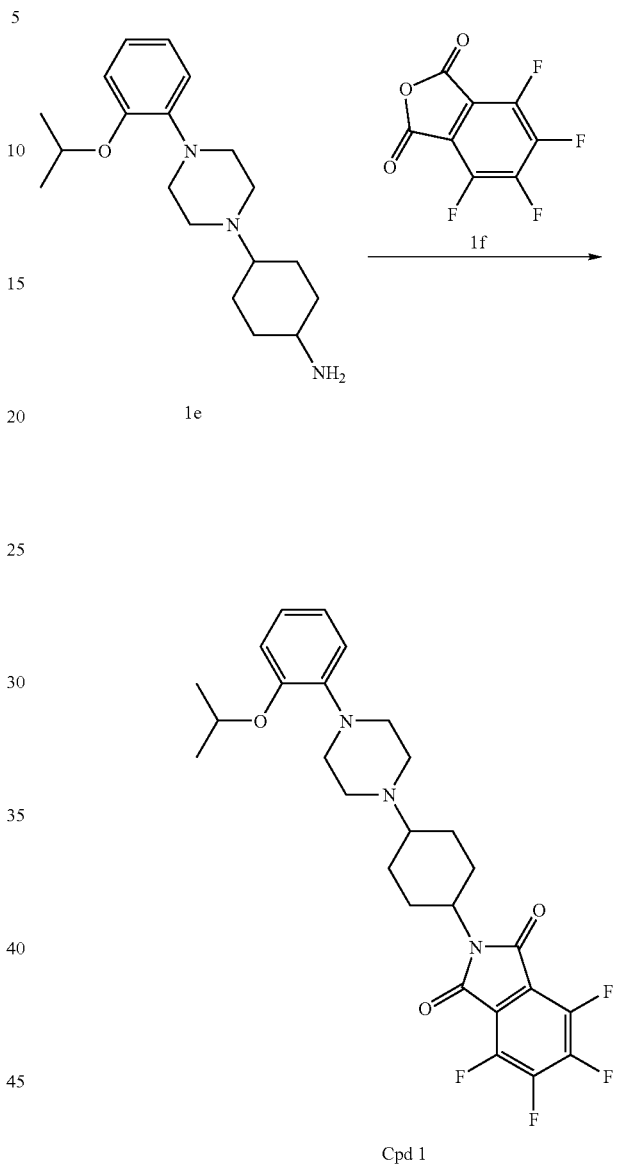

Compound 1e (0.10 g, 0.32 mmol) and 4,5,6,7-tetrafluoro-isobenzofuran-1,3-dione Compound 1f (0.070g, 0.32 mmol) were dissolved into dry benzene (10 mL). The resulting yellowish clear solution was refluxed at 80° C. for about 18 hrs. When the presence of Compound 1e as no longer detected by LC-MS, the solvent was removed using a rotary evaporator. The resulting residue was dissolved into a minimum amount of MeOH and DCM and was loaded on preparative plate (silica gel). The plate was developed in mixed solvents (5% MeOH/DCM) to provide a cis and trans mixture of Compound 1 as a yellowish oil. MS m/z 520.0 (M⁺H); $^1$H NMR (CDCl₃, TMS) δ 1.36 (d, J=6 Hz, 6H), 1.42-1.60 (m, 2H), 1.60-1.93 (m, 5H), 2.00-2.58 (m, 4H), 2.65-2.88 (m, 3H), 2.95-3.28 (m, 3H), 4.00-4.20 (m, 1H), 4.50-4.70 (m, 1H), 6.8-7.05 (m, 4H).

Following the procedure of Example 1 substituting the appropriate starting materials, reagents and solvents, the following compounds were prepared:

| Cpd | Name | MS | Ret. |
|---|---|---|---|
| 2 | 5,6-dichloro-2-{4-[4-(2-isopropoxy-phenyl)-piperazin-1-yl]-cyclohexyl}-isoindole-1,3-dione | 516 | — |
| 3 | 4-fluoro-r-2-{t-4-[4-(2-isopropoxy-phenyl)-piperazin-1-yl]-cyclohexyl}-isoindole-1,3-dione | 466 | — |
| 4 | 4-fluoro-r-2-{c-4-[4-(2-isopropoxy-phenyl)-piperazin-1-yl]-cyclohexyl}-isoindole-1,3-dione | 466 | — |
| 5 | 6-{4-[4-(2-isopropoxy-phenyl)-piperazin-1-yl]-cyclohexyl}-pyrrolo[3,4-b]pyridine-5,7-dione | 449 | 2.860 |
| 6 | 2-{4-[4-(2-isopropoxy-phenyl)-piperazin-1-yl]-cyclohexyl}-pyrrolo[3,4-c]pyridine-1,3-dione | 449 | — |
| 7 | 2-{4-[4-(2-isopropoxy-phenyl)-piperazin-1-yl]-cyclohexyl}-benzo[e]isoindole-1,3-dione | 498 | 3.318 |
| 8 | 8-fluoro-r-2-{c-4-[4-(2-isopropoxy-phenyl)-piperazin-1-yl]-cyclohexyl}-benzo[e]isoindole-1,3-dione | 516 | 3.375 |
| 9 | 8-fluoro-r-2-{t-4-[4-(2-isopropoxy-phenyl)-piperazin-1-yl]-cyclohexyl}-benzo[e]isoindole-1,3-dione | 516 | 3.188 |

BIOLOGICAL EXAMPLES $\alpha_1$-Adrenergic Receptor Binding Assay

Preparation of COS Cell Membranes

Membranes were prepared from COS-7 cells (African Green monkey kidney SV40-transformed cells) that had been transfected with one of the three $\alpha_1$-AR subtypes (Genbank accession number for the $\alpha_{1a}$ subtype: AF013261; Genbank accession number for the $\alpha_{1b}$ subtype: NM000679; Genbank accession number for the $\alpha_{1d}$ subtype: NM000678) using the following method: COS cells from ten 100 mm tissue culture plates were scraped into a 5 mL volume of TE (a mixture of 50 mM Tris-HCl, 5 mM EDTA, pH 7.4). The cell suspension was disrupted with a Brinkman Polytron (at a setting of 8) for 10 sec. The disrupted cells were centrifuged at 1000×g for 10 min at 4° C. Supernatants were centrifuged at 34,500×g for 20 min at 4° C. The membrane pellets were suspended in a 2 mL volume of TNE (a mixture of 50 mM Tris-HCl, 5 mM EDTA and 150 mM NaCl at pH 7.4). An aliquot of the membrane suspension was stored at –70° C. until use. The protein concentration was determined using the BioRad "DC" protein assay kit following membrane solubilization with Triton X-100.

Radio-Ligand Binding Assay

Triplicate determinations of radio-ligand binding in the presence of increasing concentrations of testing compound were made. The reagents were added to 96-well polypropylene plate wells. Each assay well contained 140 µL TNE, 25 µL $^{125}$I-2-(β-4-hydroxyphenyl)ethylaminomethyltetralone ($^{125}$I-HEAT) (specific activity 2200 Ci/mmol, Dupont-New England Nuclear, 50 pM final), 10 µL testing compound dissolved in dimethyl sulfoxide (DMSO) (1 pM to 10 µM in half-log increments, final), and 25 µL appropriate $\alpha_1$-AR membrane subtype suspension in TNE (0.5 ng/µL for the $\alpha_{1a}$ and $\alpha_{1b}$ subtypes and 13 ng/µL for the $\alpha_{1d}$ subtype). The plate was incubated at rt for 1 hr. The contents of the wells were filtered through a glass filter (type C) (GF/C) membrane Unifilter plate (Packard Instruments) using the Packard Filtermate cell harvester. The filter plates were dried in a vacuum oven for 30 min at 40° C. 25 µL Microscint 20 liquid scintillation fluid (Packard Instuments) was added to each well. The radioactive content was analyzed in the TopCount microplate scintillation counter (Packard Instruments).

Data Analysis

The $K_i$ values (in nM) shown in Table 1 were determined using GraphPad Prism software.

TABLE 1

| | Receptor Binding | | |
|---|---|---|---|
| Cpd | α1a-AR | α1b-AR | α1d-AR |
| 1 | 37.77 | 4108.00 | 30.20 |
| 2 | 2.69 | 1082.00 | 0.31 |
| 3 | 0.20 | 17.87 | 0.09 |
| 4 | 0.8729, 1.1, 0.95 | 164.3, 129, 88 | 3.243, 13.5, 28 |
| 5 | 0.75 | 44.59 | 1.45 |
| 6 | 0.43 | 22.40 | 0.77 |
| 7 | 0.58, 3 | 16, 14 | 0.27, 0.13 |
| 8 | 15 | 269 | 16.4 |
| 9 | 1.9, 5.9 | 35, 58 | 0.61, 0.3 |

In Vivo Models

The ability of a test compound to relax prostatic smooth muscle tissue in vivo may be evaluated using the prostatic intraurethral pressure (IUP) and blood pressure (MAP) in the anesthetized canine model. Alternatively, the ability of a test compound to relax prostate smooth muscle tissue in vivo may be evaluated by evaluating the prostatic intraurethral pressure (IUP) and blood pressure (MAP) in the conscious canine model.

It is to be understood that the preceding description teaches the principles of the present invention, with examples thereof, which have emphasized certain aspects. It will also be understood that the practice of the invention encompasses all of the usual variations, adaptations and modifications as come within the scope of the following claims and their equivalents. However, numerous other equivalents not specifically elaborated on or discussed may nevertheless fall within the spirit and scope of the present invention and claims and are intended to be included.

Throughout this application, various publications are cited. The disclosure of all publications or patents cited herein are entirely incorporated herein by reference as they show the state of the art at the time of the present invention and/or to provide description and enablement of the present invention. Publications refer to any scientific or patent publications, or any other information available in any media format, including all recorded, electronic or printed formats.

What is claimed is:

1. A compound and pharmaceutically acceptable salts thereof selected from the group consisting of:

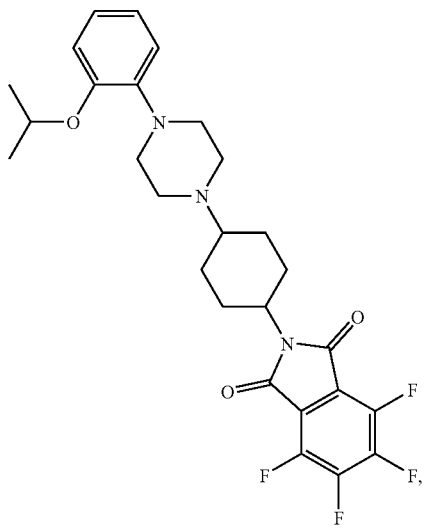

-continued
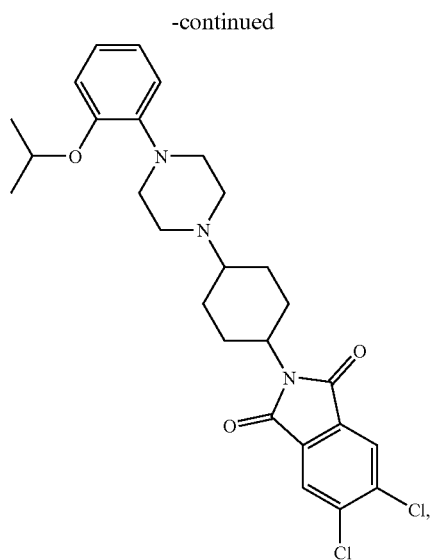
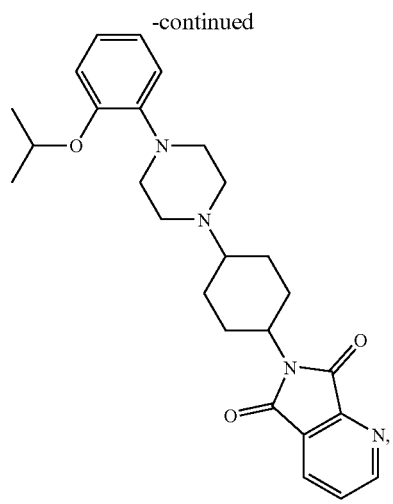
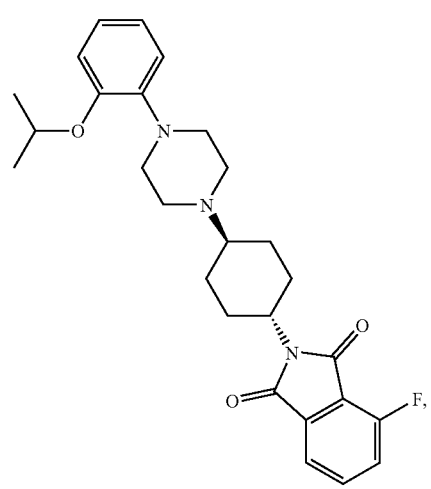
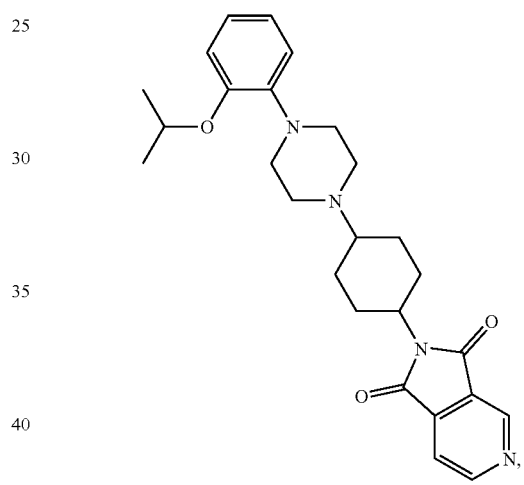
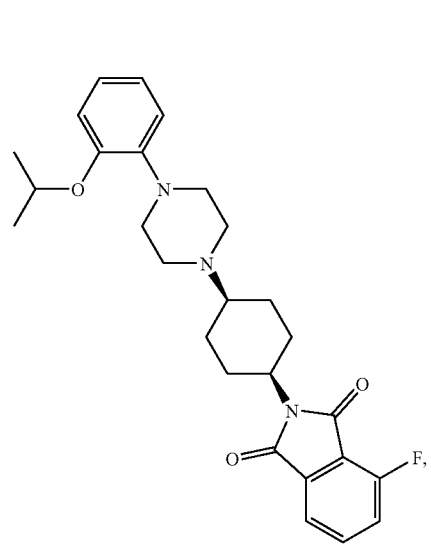
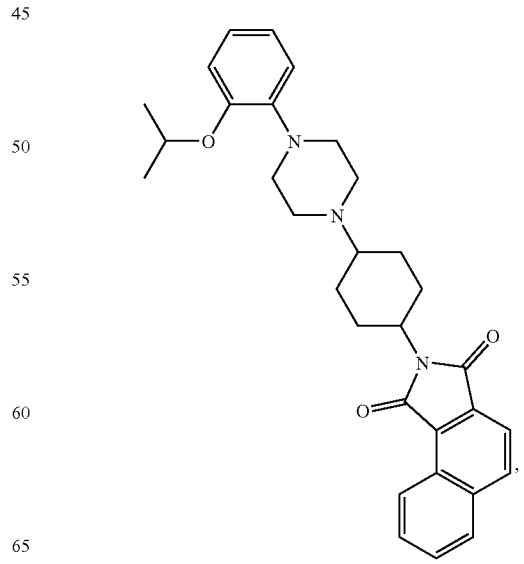

-continued

31

32 and

* * * * *